(12) United States Patent
Rao

(10) Patent No.: US 11,773,047 B2
(45) Date of Patent: Oct. 3, 2023

(54) METHOD FOR SEPARATING TRANS ISOMERIC CROCETIN FROM CIS ISOMERIC CROCETIN

(71) Applicant: Huanwen Rao, Taiwan (CN)

(72) Inventor: Huanwen Rao, Taiwan (CN)

( * ) Notice: Subject to any disclaimer, the term of this patent is extended or adjusted under 35 U.S.C. 154(b) by 440 days.

(21) Appl. No.: 17/273,314

(22) PCT Filed: Sep. 5, 2019

(86) PCT No.: PCT/CN2019/104591
§ 371 (c)(1),
(2) Date: Mar. 4, 2021

(87) PCT Pub. No.: WO2020/048516
PCT Pub. Date: Mar. 12, 2020

(65) Prior Publication Data
US 2021/0331997 A1    Oct. 28, 2021

(30) Foreign Application Priority Data

Sep. 5, 2018 (CN) .......................... 201811028776.9

(51) Int. Cl.
| | | |
|---|---|---|
| *C07C 51/43* | (2006.01) | |
| *C07C 51/50* | (2006.01) | |
| *C07C 51/41* | (2006.01) | |
| *C07B 63/04* | (2006.01) | |

(52) U.S. Cl.
CPC ............. *C07C 51/43* (2013.01); *C07C 51/412* (2013.01); *C07C 51/50* (2013.01); *C07B 63/04* (2013.01); *C07B 2200/09* (2013.01)

(58) Field of Classification Search
None
See application file for complete search history.

(56) References Cited

FOREIGN PATENT DOCUMENTS

| | | |
|---|---|---|
| CN | 104402702 | 3/2015 |
| CN | 103073417 | 9/2015 |
| CN | 105907807 | 8/2016 |
| CN | 106905145 | 6/2017 |
| CN | 109180469 | 1/2019 |
| JP | 2011168649 | 9/2011 |

OTHER PUBLICATIONS

"International Search Report (Form PCT/ISA/210) of PCT/CN2019/104591," dated Dec. 3, 2019, with English translation thereof, pp. 1-4.

*Primary Examiner* — Tam M Nguyen
(74) *Attorney, Agent, or Firm* — JCIP GLOBAL INC.

(57) ABSTRACT

A method for separating trans isomer crocetin from cis isomer crocetin is provided. The method comprises crystallizing all-trans crocetin with calcium ions first by using different binding capabilities between cis and trans isomeric crocetin to calcium ions and acidifying the all-trans crocetin to obtain 13-cis crocetin.

11 Claims, 9 Drawing Sheets

METHOD FOR SEPARATING TRANS ISOMERIC CROCETIN FROM CIS ISOMERIC CROCETIN

CROSS-REFERENCE TO RELATED APPLICATION

This application is a 371 of international application of PCT application serial no. PCT/CN2019/104591, filed Sep. 5, 2019, which claims the priority benefit of China application no. 201811028776.9, filed on Sep. 5, 2018. The entirety of each of the above mentioned patent applications is hereby incorporated by reference herein and made a part of this specification.

BACKGROUND

The invention belongs to the technical field of natural medicine chemistry and relates to the technical field of extraction and separation of natural plant active ingredients, in particular to a method for separating trans isomeric crocetin from cis isomeric crocetin.

Crocetin is a carotenoid compound, is generally present in plants in the form of gentiobiose (i.e., crocin), and is mainly distributed in saffron and *gardenia*. Crocetin has strong antioxidation, cardiovascular protection, and skin cancer suppression effects [1] and has potential application value in medicine and skin care products. When studying the effects of UVA on human skin fibroblasts, Ohba T[2] found out that crocetin may protect human skin fibroblasts from UVA damage. The mechanism is that crocetin may reduce the production of active oxygen caused by UVA. When studying the effects of crocetin on scleroderma in mice caused by bleomycin, Yinghua Song [3] found out that crocetin may reverse skin fibrosis.

Saffron contains higher crocin and crocetin, but saffron is expensive, and the costs of preparing crocetin from saffron is considerable. *Gardenia jasminoides* ellis fruit is cheap and abundant, providing rich sources of raw materials for crocetin. Studies show that the aglycon of crocin in *Gardenia jasminoides* ellis fruit, namely crocetin, has two structures, that is, all-trans (E-crocetin) and 13-cis (Z-crocetin) [4]. Generally, crude crocetin may be prepared from *gardenia* yellow (the main ingredient is crocin) through alkali-solution and acid-isolation. Generally, the purity ranges from 50% to 80%, and it is difficult to separate the two to obtain high-purity crocetin. In patent CN201310066851.1, pyridine is used as a solvent to prepare high-purity trans-crocetin by recrystallization, but the pyridine used in this method is highly toxic. In patent CN201410666585.0, a silica gel column is used to purify *gardenia* yellow to obtain high-purity crocin, the high-purity crocin is then used as the raw material to prepare crocetin, and N,N-dimethylformamide is finally recrystallized to obtain high-purity crocetin. Such process is complicated, and the silica gel column chromatography used is difficult to be industrialized. In patent CN201610292072.7, an anhydrous ethanol recrystallization method is adopted to increase the purity of crocetin from 55.5% to 96%. Nevertheless, in actual operation, it is found that crocetin is hardly soluble in ethanol, so the actual consumption of ethanol is considerably large. In patent 201710227023.X, high-concentration alkaline solution is used for recrystallization to obtain high-purity crocetin. According to Example 2, it is estimated that when 10.0 g of crocetin with a purity of 10.6% is to be recrystallized and purified of to a purity of 99.4% (0.93 g), more than 100 g of potassium hydroxide is required to be consumed. This method consumes much alkali and may easily produce a large amount of alkaline waste liquid.

SUMMARY

The purpose of the invention is to overcome the above-mentioned defects or problems in the BACKGROUND section, so the invention provides a method for separating trans isomeric crocetin from cis isomeric crocetin.

To accomplish the foregoing purpose, the following technical solutions are adopted by the invention.

A method for separating trans isomeric crocetin from cis isomeric crocetin is provided and includes the following steps. All-trans crocetin was crystallized with calcium ions first by using different binding capabilities between cis and trans isomeric crocetin to calcium ions, and then 13-cis crocetin was obtained via acidification.

Moreover, the calcium ions in this method were derived from a soluble calcium salt solution, such as calcium acetate, calcium chloride, and calcium citrate, and a mass concentration thereof was 1% to 20%.

Moreover, the method further includes the following steps.
(1) Crude crocetin and water were placed in a beaker, pH was adjusted to 7-14 with alkali, the crude crocetin was heated to be dissolved, and insoluble matters were filtered out while hot.
(2) Calcium ions were slowly dripped into a filtrate for crocetin calcium salt to be precipitated, and precipitated crocetin calcium salt was kept warm to allow for full crystallization.
(3) The filtrate was filtered.
(4) Filter residues were washed with ethanol, acidified with acid, kept warm, filtered, washed with pure water, and vacuum dried to obtain all-trans crocetin.
(5) Acid was added to the filtrate of (3) for acidification, and the filtrate was kept warm and filtered. Filter residues were washed with pure water and vacuum dried to obtain cis-crocetin.

Moreover, the method further includes the following steps.
(1) 5 g to 50 g of crude crocetin and 500 ml to 5,000 ml of water were placed in a beaker, pH was adjusted to 8-14 with alkali, the crude crocetin was heated to be dissolved, and insoluble matters were filtered out while hot.
(2) Calcium ions were slowly dripped into a filtrate for crocetin calcium salt to be precipitated, and precipitated crocetin calcium salt was kept warm to allow for full crystallization.
(3) The filtrate was filtered.
(4) Filter residues were washed with ethanol of 50% or greater first, pH was adjusted to 3-6 with acid, and the filter residues were kept warm, filtered, washed with pure water, and vacuum dried to obtain a brick red solid, that is, the all-trans crocetin.
(5) Acid was added to the filtrate of (3), pH was adjusted to 2-5, the filtrate was kept warm to allow the filtrate to be fully precipitated (crystallized), the filtrate was filtered and filter residues were washed with pure water and vacuum dried to obtain a dark red solid, that is, the 13-cis crocetin.

Moreover, the method specifically includes the following steps.
(1) 10 g of crude crocetin and 700 mL of pure water were placed in a beaker, pH was adjusted to 11 with alkali, the crude crocetin was heated to be dissolved, and insoluble matters were filtered out while hot.
(2) 5 ml of a 5% calcium chloride solution was slowly dripped into a filtrate for crocetin calcium salt to be precipitated, and precipitated crocetin calcium salt was kept warm to allow for full crystallization.
(3) The filtrate was filtered.
(4) Filter residues were washed twice with ethanol of 50% and dispersed with 50 mL of pure water, pH was adjusted to 4-5 with citric acid, and the filter residues were kept at 60° C. for 2 hours, filtered, washed with pure water, and vacuum dried to obtain high-purity all-trans crocetin.
(5) The filtrate of (3) was acidified with citric acid until pH becomes 4-5, kept warm to age floc and filtered. Filer residues were washed with pure water and vacuum dried to obtain cis-crocetin.

Moreover, the method further includes the following steps.
(1) 20 g of crude crocetin and 1,500 mL of pure water were placed in a beaker, pH was adjusted to 11 with alkali, the crude crocetin was heated to be dissolved, insoluble matters were filtered out while hot, and a filtrate was collected.
(2) 10 ml of 5% calcium chloride was slowly dripped into the filtrate, and the filtrate was kept at 60° C. for 4 hours.
(3) The filtrate was filtered.
(4) Filter residues were washed twice with ethanol of 50% first and dispersed with 200 mL of pure water, pH was adjusted to 4-5 with acid, and the filter residues were kept at 60° C. for 2 hours, filtered, washed with pure water, and vacuum dried to obtain high-purity all-trans crocetin.
(5) Acid was added to the filtrate of (3) until pH becomes 4-5, the filtrate was kept warm for 2 hours and filtered. Filter residues were washed with pure water and vacuum dried to obtain 13-cis crocetin.

Moreover, the alkali used is a soluble alkali solution, such as sodium hydroxide and potassium hydroxide, and the acid used is an acid that does not form a precipitate with calcium ions, such as hydrochloric acid and citric acid.

Based on the above description provided by the invention, it can be seen that compared to the related art, the principle of the method provided by the invention is to use the molecular structure differences between cis-/trans-crocetin. All-trans crocetin is prone to form regular molecular complexes with $Ca^{2+}$ ions, that is, precipitation (crystallization) easily occurs, while cis-crocetin is not easy to form regular molecular complexes with $Ca^{2+}$, that is, cis-crocetin is not easy to form precipitate with $Ca^{2+}$. According such differences, the cis-trans isomers of crocetin may be separated simultaneously to prepare high-purity all-trans crocetin.

BRIEF DESCRIPTION OF THE DRAWINGS

To make the technical solutions provided in the embodiments of the invention more clearly illustrated, several accompanying drawings required by the embodiments for description are briefly introduced as follows. Obviously, the drawings in the following description are only some embodiments of the invention, and for a person having ordinary skill in the art, other drawings can be obtained based on these drawings without inventive effort.

DESCRIPTION OF THE EMBODIMENTS

Figure 1:
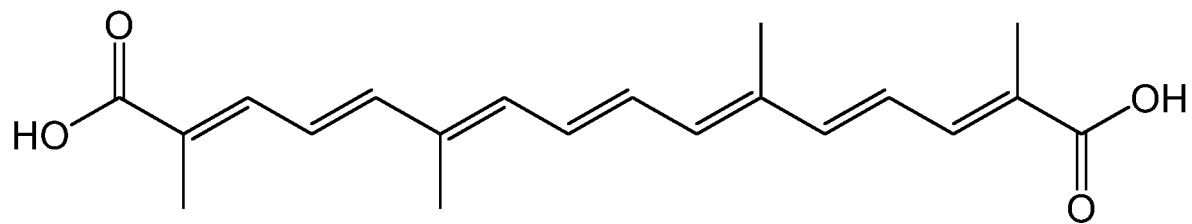
FIG. 1 is a molecular structure of all-trans crocetin (E-crocetin).

The accompanying drawings in the embodiments of the invention are included to provide a clear and complete description of the technical solutions provided in the embodiments of the invention. Obviously, the described embodiments are preferred embodiments of the invention, and should not be regarded as exclusion of other embodiments. Based on the embodiments of the invention, all other embodiments obtained by a person of ordinary skill in the art without making any inventive effort fall within the scope that the invention seeks to protect.

Unless otherwise clearly defined in the claims, specification, and the above-mentioned drawings of the invention, the terms "first", "second", or "third" and so on are used to distinguish different objects, not used to describe a specific order.

Unless otherwise clearly defined in the claims, specification, and the above-mentioned drawings of the invention, for location words, such as the use of the terms "center", "transverse", "perpendicular", "horizontal", "vertical", "top", "bottom", "inner", "outer", "upper", "lower", "front", "rear", "left", "right", "clockwise", "counterclockwise", and other indication orientations or positional relationships are based on the orientations and positional relationships shown in the drawings, are provided to facilitate the description of the invention and simplify the description, and are not intended to indicate or imply that the indicated device or element must have a specific orientation or be constructed and operated in a specific orientation, so cannot be understood as limiting the specific protection scope of the invention.

Unless otherwise clearly defined in the claims, specification, and the above-mentioned drawings of the invention, if the term "fixedly connected" or "fixed connection" is used, it should be understood in a broad sense, that is, no connection manner of a displacement relationship and a relative rotation relationship is provided therebetween. That is, non-detachable fixed connection, detachable fixed connection, integrated connection, and fixed connection through other devices or elements are included.

In the claims, specification, and the above-mentioned drawings of the invention, if the words "include", "have", and variations thereof are used, it is intended to indicate "include but not be limited to".

With reference to FIGS. 1-10, a method for separating trans isomeric crocetin from cis isomeric crocetin is provided and includes the following steps. All-trans crocetin was crystallized with calcium ions first by using different binding capabilities between cis and trans isomeric crocetin to calcium ions, and then 13-cis crocetin was obtained via acidification.

Moreover, the calcium ions in this method were derived from a soluble calcium salt solution, such as calcium acetate, calcium chloride, and calcium citrate, and a mass concentration thereof was 1% to 20%.

Moreover, the method further includes the following steps.
(1) Crude crocetin and water were placed in a beaker, pH was adjusted to 7-14 with alkali, the crude crocetin was heated to be dissolved, and insoluble matters were filtered out while hot.
(2) Calcium ions were slowly dripped into a filtrate for crocetin calcium salt to be precipitated, and precipitated crocetin calcium salt was kept warm to allow for full crystallization.
(3) The filtrate was filtered.
(4) Filter residues were washed with ethanol, acidified with acid, kept warm, filtered, washed with pure water, and vacuum dried to obtain all-trans crocetin.
(6) Acid was added to the filtrate of (3) for acidification, and the filtrate was kept warm and filtered. Filer residues were washed with pure water and vacuum dried to obtain cis-crocetin.

Moreover, the method further includes the following steps.
(1) 5 g to 50 g of crude crocetin and 500 ml to 5,000 ml of water were placed in a beaker, pH was adjusted to 8-14 with alkali, the crude crocetin was heated to be dissolved, and insoluble matters were filtered out while hot.
(2) Calcium ions were slowly dripped into a filtrate for crocetin calcium salt to be precipitated, and precipitated crocetin calcium salt was kept warm to allow for full crystallization.
(3) The filtrate was filtered.
(4) Filter residues were washed with ethanol of 50% or greater first, pH was adjusted to 3-6 with acid, and the filter residues were kept warm, filtered, washed with pure water, and vacuum dried to obtain a brick red solid, that is, the all-trans crocetin.
(5) Acid was added to the filtrate of (3), pH was adjusted to 2-5, the filtrate was kept warm to allow the filtrate to be fully precipitated (crystallized), the filtrate was filtered. Filter residues were washed with pure water and vacuum dried to obtain a dark red solid, that is, the 13-cis crocetin.

Specific steps are provided as follows.
(1) 10 g of crude crocetin and 700 mL of pure water were placed in a beaker, pH was adjusted to 11 with alkali, the crude crocetin was heated to be dissolved, and insoluble matters were filtered out while hot.
(2) 5 ml of a 5% calcium chloride solution was slowly dripped into a filtrate for crocetin calcium salt to be precipitated, and precipitated crocetin calcium salt was kept warm to allow for full crystallization.
(3) The filtrate was filtered.
(4) Filter residues were washed twice with ethanol of 50% and dispersed with 50 mL of pure water, pH was adjusted to 4-5 with citric acid, and the filter residues were kept at 60° C. for 2 hours, filtered, washed with pure water, and vacuum dried to obtain high-purity all-trans crocetin.
(5) The filtrate of (3) was acidified with citric acid until pH becomes 4-5, kept warm to age floc and filtered. Filter residues were washed with pure water and vacuum dried to obtain cis-crocetin.

Embodiment One (1) 20 g of crude crocetin (tested E-crocetin content was 62%, and Z-crocetin content was 8.3%) and 1,500 mL of pure water were poured in a beaker, pH was adjusted to 11 with sodium hydroxide base, the crude crocetin was heated to be dissolved, and insoluble matters were filtered out while hot.
(2) 10 ml of 5% calcium chloride was slowly dripped into a filtrate, and the filtrate was kept at 60° C. for 4 hours.
(3) The filtrate was filtered.
(4) Filter residues were washed twice with ethanol of 75%, acidified with 200 mL of 1% citric acid, kept at 60° C. for 2 hours, filtered, washed with pure water, and vacuum dried to obtain 12.1 g of all-trans crocetin (detected by HPLC, the purity was 97%).
(5) 5% of citric acid was added to the filtrate of (3) until pH becomes 4, the filtrate was kept warm for 2 hours and filtered. Filter residues were washed with pure water and vacuum dried to obtain 1.62 g of cis crocetin (detected by HPLC, the purity was 94%).

Embodiment Two (1) 100 g of *gardenia* yellow (a color value is 405) and 800 mL of pure water were placed in a beaker and heated to 70° C. to be completely dissolved. 50 mL of 20% sodium hydroxide was slowly added into a *gardenia* yellow solution, and the *gardenia* yellow solution was continuously stirred, kept at 60° C., and reacted for 30 minutes. 10% of hydrochloric acid was added and dripped into a reaction solution until pH becomes 4, the reaction solution was kept warm for 1 hour to allow a precipitate to age and was extracted and filtered, the filter residues were washed twice with pure water, and a dark red solid (i.e., the crude crocetin after drying) was obtained.
(2) The dark red solid in (1) and 1,000 mL of pure water were transferred into a beaker, added with 10% of sodium hydroxide to allow pH to be adjusted to 10-11, heated to be dissolved, and filtered to remove insoluble matters.
(3) 4 mL of a 5% $CaCl_2$) solution was slowly added, and the filtrate was kept at 60° C. for 4 hours.
(4) The filtrate was filtered.
(5) Filter residues were washed twice with ethanol of 80%, acidified with 150 mL of 1% citric acid, kept at 60° C. for 2 hours, filtered, washed with pure water, and vacuum dried to obtain 10.63 g of all-trans crocetin (detected by HPLC, the purity was 97%).
(6) 5% of citric acid was added to the filtrate of (4) until pH becomes 3-4, the filtrate was kept warm for 2 hours and filtered. Filter residues were washed with pure water and vacuum dried to obtain 1.53 g of cis crocetin (detected by HPLC, the purity was 93%).

In the invention, the alkali used is a soluble alkali solution, such as sodium hydroxide and potassium hydroxide, and the acid used is an acid that does not form a precipitate with calcium ions, such as hydrochloric acid and citric acid.

Figure 2:
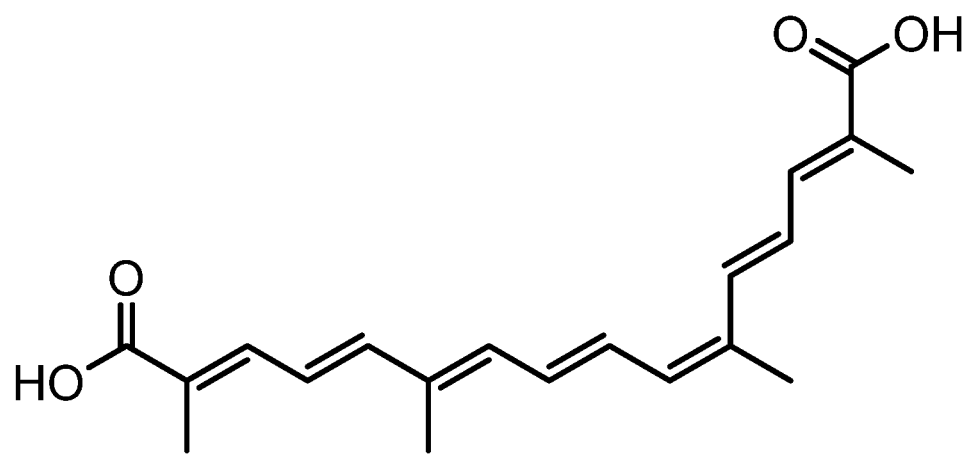
FIG. 2 is a molecular structure of 13-cis crocetin (13Z-crocetin).
Figure 3:
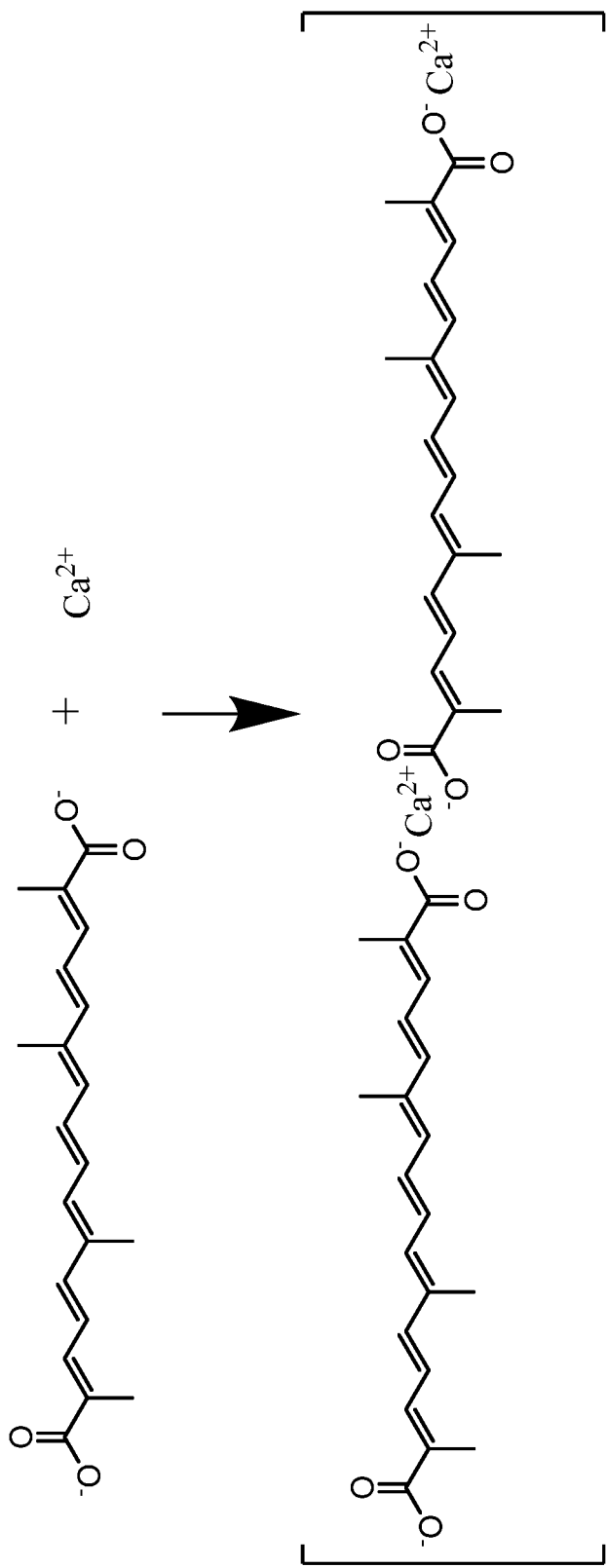
FIG. 3 is a schematic diagram showing that E-crocetin can form a precipitate with $Ca^{2+}$.
Figure 4:
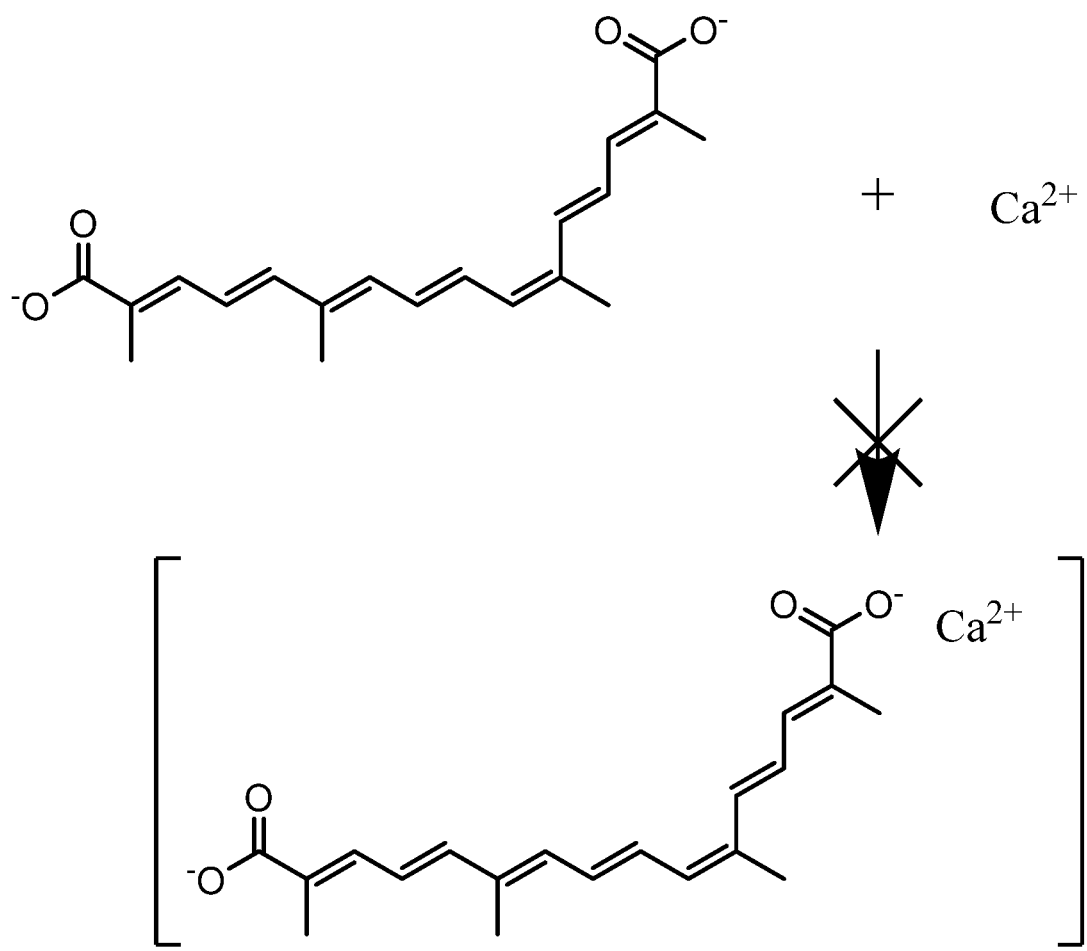
FIG. 4 is a schematic diagram showing that 13Z-crocetin cannot form a precipitate with $Ca^{2+}$.

FIG. 1 is a schematic diagram of a molecular structure of all-trans crocetin (E-crocetin), FIG. 2 is a schematic diagram of a molecular structure of 13-cis crocetin, and FIG. 3 is a schematic diagram of precipitation formed between all-trans crocetin (E-crocetin) and $Ca^{2+}$ ions. The molecular complex structures formed by all-trans crocetin and $Ca^{2+}$ ions are regular, so crystallization (precipitation) may easily occur. That is, all-trans crocetin may be precipitated by $Ca^{2+}$. The molecular complex structures formed by 13Z-crocetin and $Ca^{2+}$ ions are not regular, so 13Z-crocetin is not sensitive to $Ca^{2+}$ ions and does not co-precipitate with $Ca^{2+}$.

The following experiment is conducted to prove effectiveness of the invention.

(I) Analysis of Crocetin by UV-Vis

Methods:

0.02 g (accurate to 0.0001 g) was added into a beaker, 50 ml of anhydrous ethanol was added, ultrasound was introduced for dissolution, and the solution was transferred to a 100 mL volumetric flask, diluted with anhydrous ethanol, shaken well, removed by 1.00 ml from the 100 ml volumetric flask, diluted to the mark with anhydrous ethanol, and shaken well. The solution was scanned 210 nm-700 nm absorption spectrum with an ultraviolet spectrophotometer.

Figure 5:
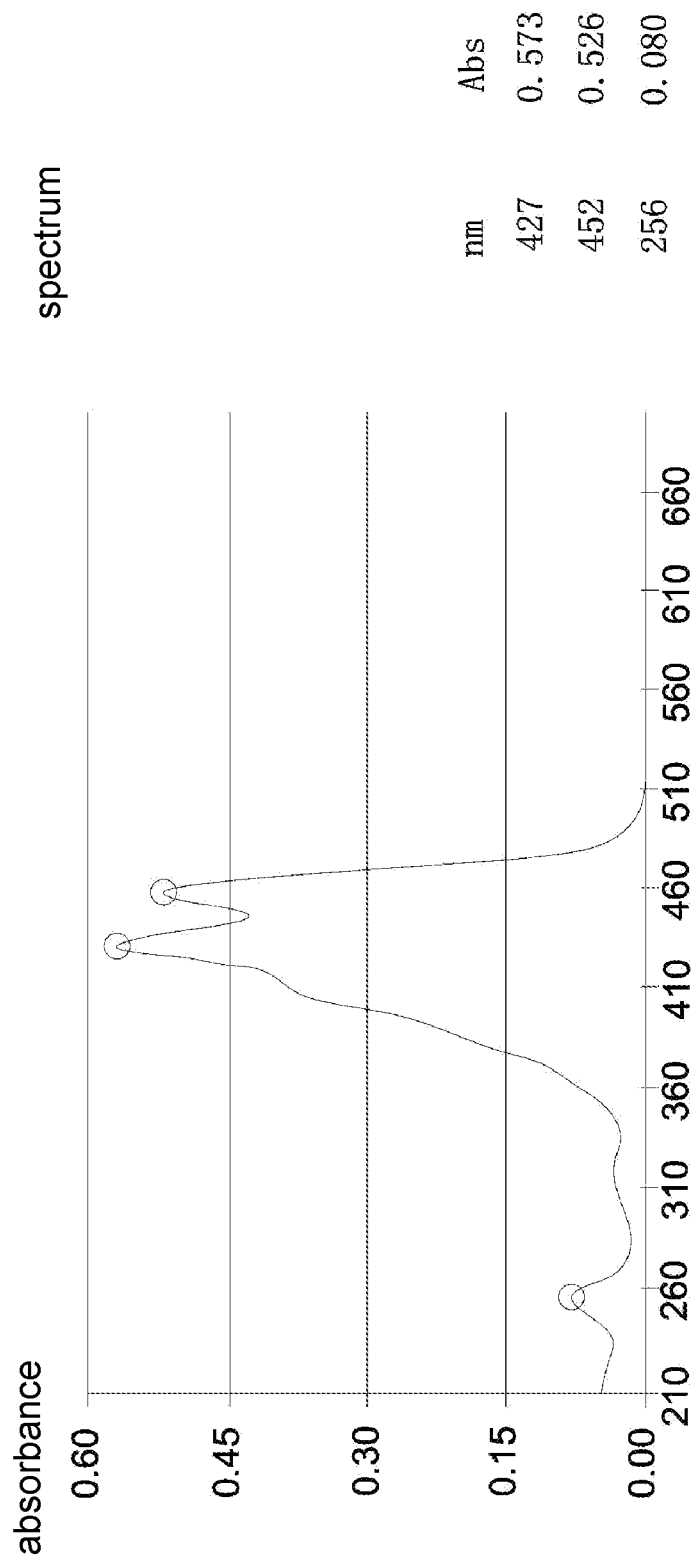
FIG. 5 is a spectrum of all-trans crocetin (E-crocetin).
Figure 6:
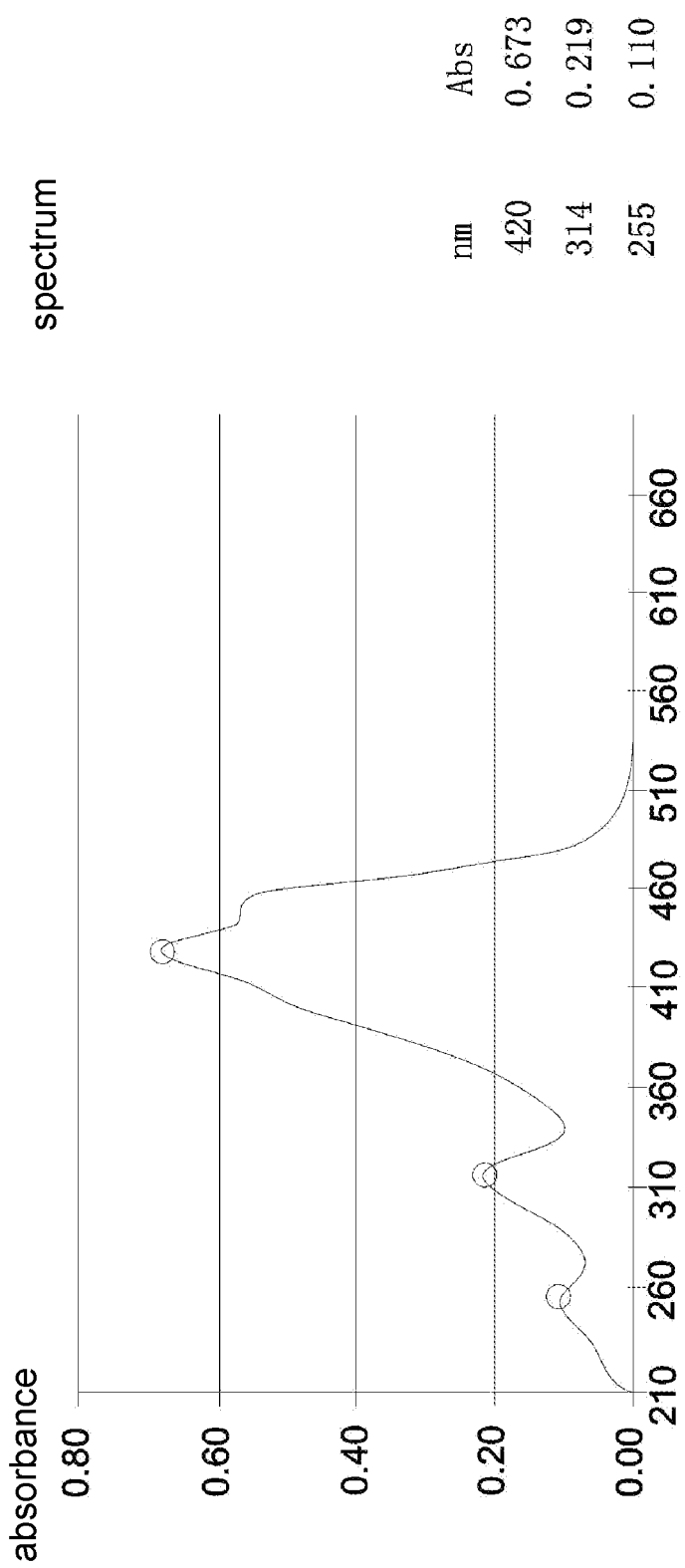
FIG. 6 is a spectrum of 13Z-crocetin (13z-crocetin).

FIG. 5 and FIG. 6 may be referenced to for the results.

The spectrum is provided as follows after ultraviolet spectrophotometer scanning is performed. Herein, the absorption peaks of E-crocetin in methanol are 427 nm, 452 nm, and 256 nm, and the absorption peaks of 13Z-crocetin in methanol are 420 nm, 314 nm, and 255 nm. According to the characteristic absorption spectra of carotenoid, the absorption peak near 320 nm is the characteristic peak of carotenoid with 13Z-cis structure. That is, it is verified from another aspect that in the process provided by the invention, trans isomeric crocetin may be effectively separated from cis isomeric crocetin.

(II) Analysis of Crocetin by HPLC-DAD

Methods:

0.01 g (accurate to 0.0001 g) was added into a beaker, 50 ml of anhydrous ethanol was added, ultrasound was introduced for dissolution, and the solution was transferred to a 100 mL volumetric flask, diluted with anhydrous ethanol, and shaken well, a small amount of the solution was filtered with a 0.45 μm microporous filter, and the filtrate was analyzed by HPLC-DAD.

Instrument conditions: Shimadzu LC-16 liquid chromatography system; C18 chromatographic column (WondaSil C18-WR 5 μm, 4.6×150 mm); DAD detector (SPD-M20A); SIL-16 auto sampler.

Chromatographic conditions: fluidity A methanol; fluidity B 0.1% phosphoric acid; system program, 40% A→100% A (40 minutes); detection wavelength 210 nm, 426 nm; column oven: 40° C.

Figure 7:
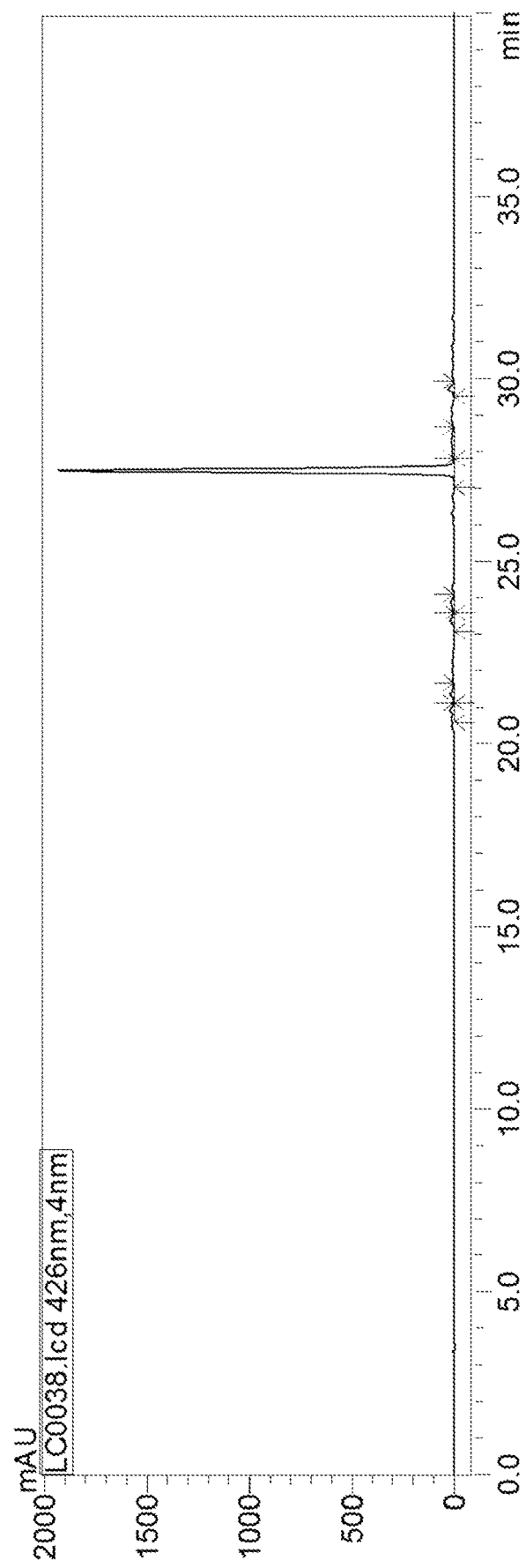
FIG. 7 is a chromatogram of all-trans crocetin (E-crocetin).
Figure 8:
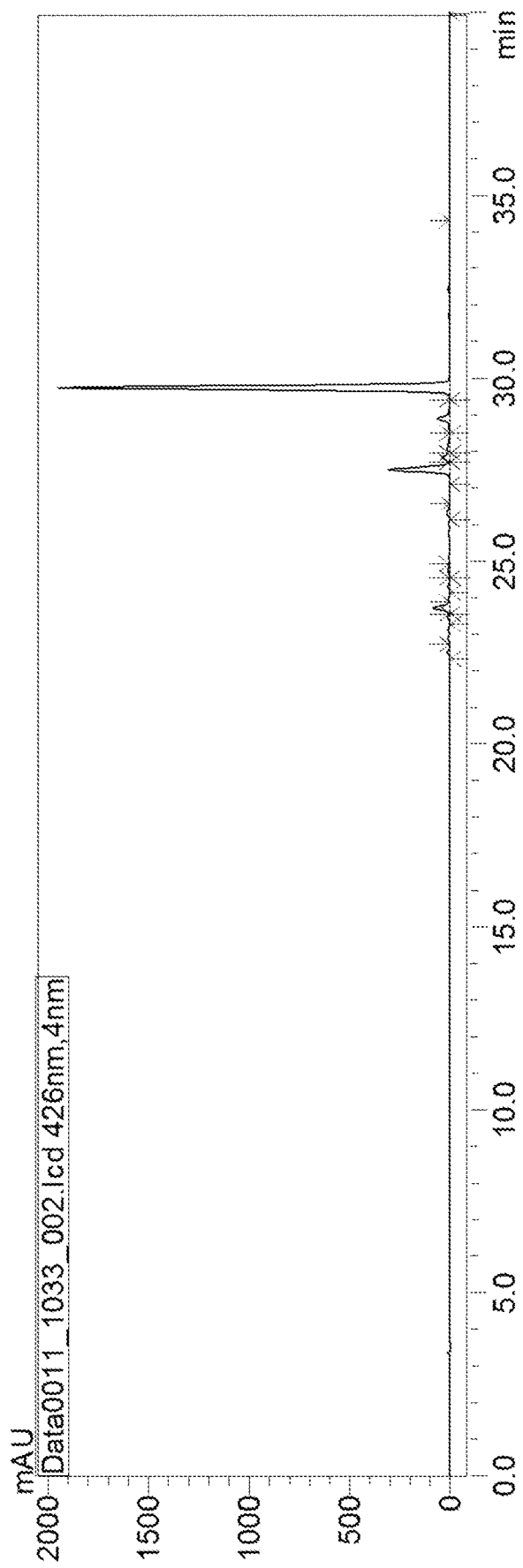
FIG. 8 is a chromatogram of 13Z-crocetin (13z-crocetin).

Results:

FIG. 7 is an HPLC chromatogram of E-crocetin prepared in Embodiment 1, and in the figure, the retention time of the main peak is 27.7 min, and the peak area accounts for 97%. FIG. 8 is an HPLC chromatogram of 13Z-crocetin prepared in Embodiment 1, and in the figure, the retention time of the main peak is 29.9 min, the peak area accounts for 93%, the retention time of the secondary peak is 27.7 min, and the peak area accounts for 6%.

III. NMR Characterization of Crocetin

Figure 9:
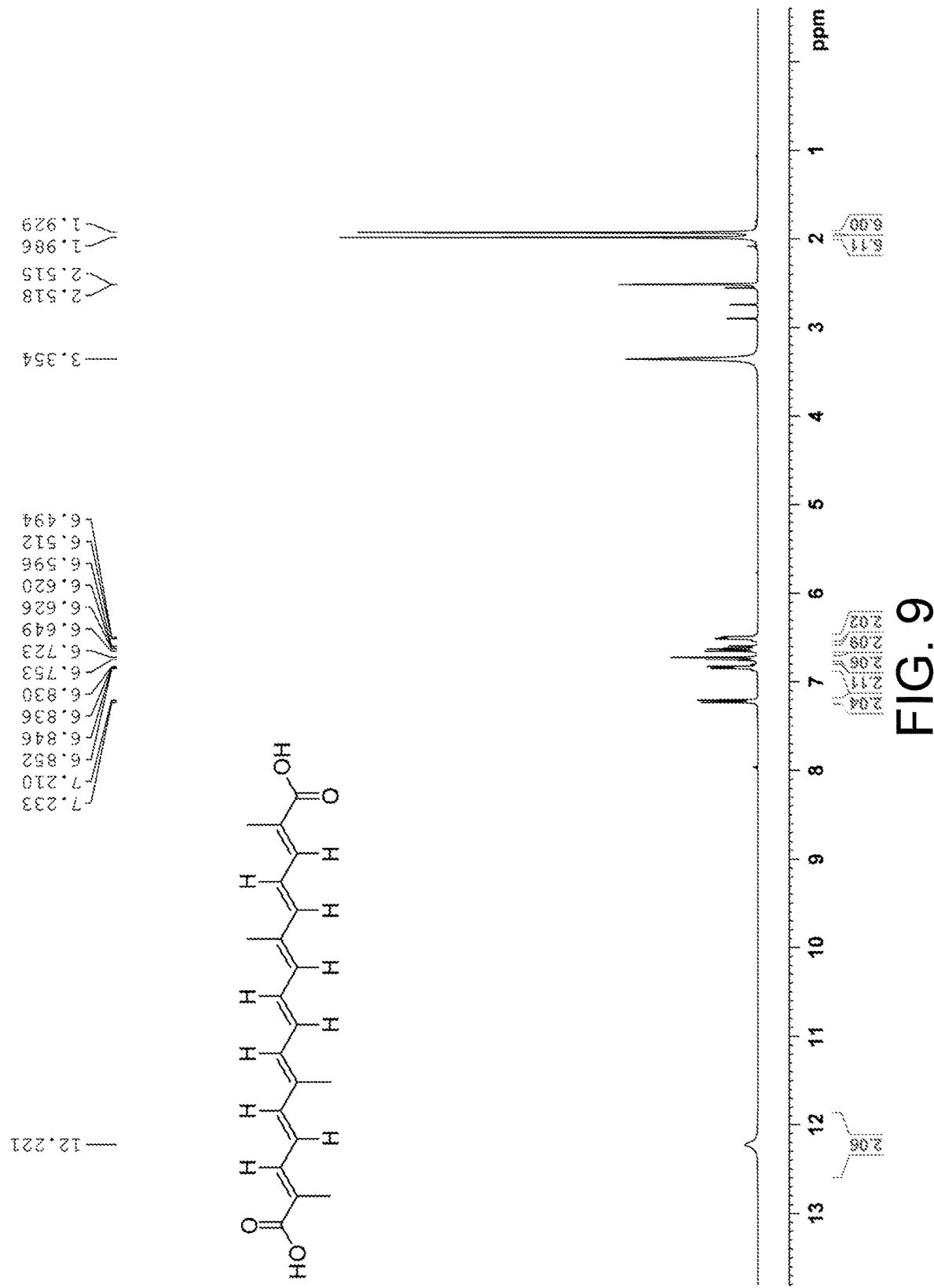
FIG. 9 is H-NMR (DMSO-d6, 500 MHz) of all-trans crocetin (E-crocetin).
Figure 10:
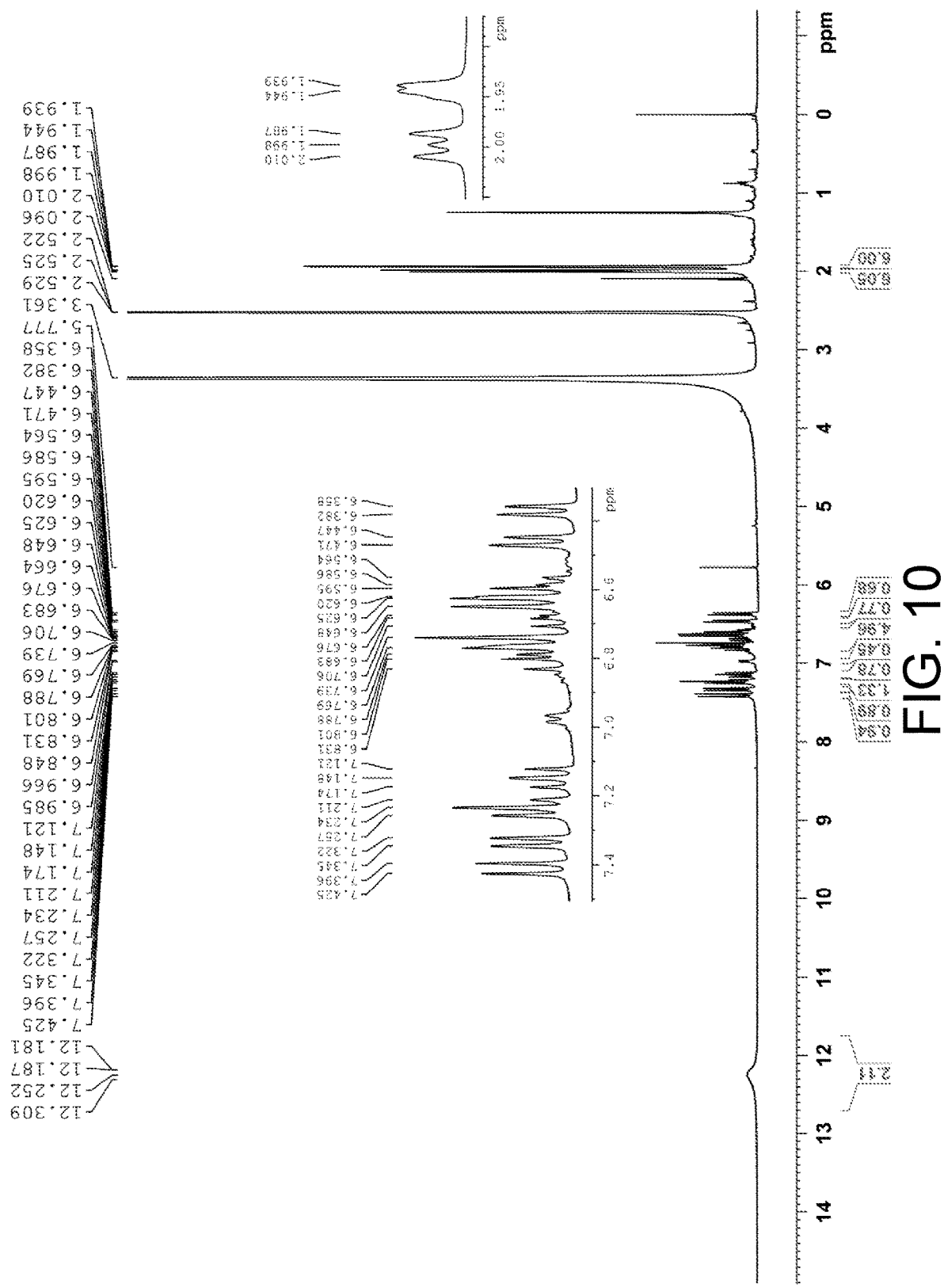
FIG. 10 is H-NMR of 13Z-crocetin (DMSO-d6, 500 MHz).

The all-trans crocetin and 13-cis crocetin are analyzed by H-NMR, and the spectra obtained after processing are shown in FIGS. 9 and 10. Through comparison with literature[5], it is confirmed that the samples separated in the invention are all-trans crocetin (FIG. 1) and 13-cis crocetin (FIG. 2).

The principle of the method provided by the invention is to use the molecular structure differences between cis-/trans-crocetin. All-trans crocetin is prone to form regular molecular complexes with $Ca^{2+}$ ions, that is, precipitation (crystallization) easily occurs, while cis-crocetin is not easy to form regular molecular complexes with $Ca^{2+}$, that is, cis-crocetin is not easy to form precipitate with $Ca^{2+}$. According such differences, the cis-trans isomers of crocetin may be separated simultaneously to prepare high-purity all-trans crocetin.

The crocetin precipitant used in the embodiments of the invention is $Ca^{2+}$, and many related metal ion chemicals may alternatively be used, which are not listed here.

Although the description of the specification and embodiments provided above serve to explain the scope of the invention, such description should not be construed as limitations on the scope of the invention. Through inspiration provided by the invention or the embodiments, modifications, equivalents, or other improvements of the embodiments or part of the technical features of the invention obtained by a person having ordinary skill in the art by combining general knowledge and common technical knowledge in the art and/or related art through logical analyses, reasoning, or limited tests fall within the protection scope of the invention.

What is claimed is:

1. A method for separating trans isomeric crocetin from cis isomeric crocetin, comprising: crystallizing all-trans crocetin with calcium ions first by using different binding capabilities between cis and trans isomeric crocetin to calcium ions and, obtaining 13-cis crocetin via acidification.

2. The method for separating trans isomeric crocetin from cis isomeric crocetin according to claim 1, wherein the calcium ions in this method are derived from a soluble calcium salt solution, such as calcium acetate, calcium chloride, and calcium citrate, and a mass concentration thereof is 1% to 20%.

3. The method for separating trans isomeric crocetin from cis isomeric crocetin according to claim 1, wherein the method includes the following steps:
    (1) placing crude crocetin and water in a beaker, adjusting pH to 7-14 with alkali, heating to dissolve the crude crocetin, filtering out insoluble matters while hot;
    (2) slowly dripping calcium ions into a filtrate for crocetin calcium salt to be precipitated, keeping precipitated crocetin calcium salt warm to allow for full crystallization;
    (3) filtering the filtrate;
    (4) washing filter residues with ethanol, acidifying the filter residues with acid, keeping the filter residues warm, filtering the filter residues, washing the filter residues with pure water, vacuum drying the filter residues to obtain all-trans crocetin; and
    (5) adding acid to the filtrate of (3) for acidification, keeping the filtrate warm, filtering the filtrate, washing the filter residues with pure water, vacuum drying the filter residues to obtain cis-crocetin.

4. The method for separating trans isomeric crocetin from cis isomeric crocetin according to claim 3, wherein the method further includes the following steps:
    (1) placing 5 g to 50 g of crude crocetin and 500 ml to 5,000 ml of water in a beaker, adjusting pH to 8-14 with alkali, heating to dissolve the crude crocetin, filtering out insoluble matters while hot;
    (2) slowly dripping calcium ions into a filtrate for crocetin calcium salt to be precipitated, keeping precipitated crocetin calcium salt warm to allow for full crystallization;
    (3) filtering the filtrate;
    (4) washing filter residues with ethanol of 50% or greater first, adjusting pH to 3-6 with acid, keeping the filter residues warm, filtering the filter residues, washing the filter residues with pure water, vacuum drying the filter residues to obtain a brick red solid, that is, the all-trans crocetin; and (5) adding acid to the filtrate of (3), adjusting pH to 2-5, keeping the filtrate warm to allow the filtrate to be fully precipitated (crystallized), filtering the filtrate, washing the filter residues with pure water, vacuum drying the filter residues to obtain a dark red solid, that is, the 13-cis crocetin.

5. The method for separating trans isomeric crocetin from cis isomeric crocetin according to claim 4, wherein the method specifically includes the following steps:

(1) placing 10 g of crude crocetin and 700 mL of pure water in a beaker, adjusting pH to 11 with alkali, heating to dissolve the crude crocetin, filtering out insoluble matters while hot;

(2) slowly dripping 5 ml of a 5% calcium chloride solution into a filtrate for crocetin calcium salt to be precipitated, keeping precipitated crocetin calcium salt warm to allow for full crystallization;

(3) filtering the filtrate;

(4) washing filter residues twice with ethanol of 50%, dispersing the filter residues with 50 mL of pure water, adjusting pH to 4-5 with citric acid, keeping the filter residues at 60° C. for 2 hours, filtering the filter residues, washing the filter residues with pure water, vacuum drying the filter residues to obtain high-purity all-trans crocetin; and (5) acidifying the filtrate of (3) with citric acid until pH becomes 4-5, keeping the filtrate warm to age floc, filtering the filtrate, washing the filter residues with pure water, vacuum drying the filter residues to obtain cis-crocetin.

6. The method for separating trans isomeric crocetin from cis isomeric crocetin according to claim 4, wherein the method further includes the following steps:

(1) placing 20 g of crude crocetin and 1,500 mL of pure water in a beaker, adjusting pH to 11 with alkali, heating to dissolve the crude crocetin, filtering out insoluble matters while hot, collecting a filtrate;

(2) slowly dripping 10 ml of 5% calcium chloride into the filtrate, keeping the filtrate at 60° C. for 4 hours;

(3) filtering the filtrate;

(4) washing filter residues twice with ethanol of 50% first, dispersing the filter residues with 200 mL of pure water, adjusting pH to 4-5 with acid, keeping the filter residues at 60° C. for 2 hours, filtering the filter residues, washing the filter residues with pure water, vacuum drying the filter residues to obtain high-purity all-trans crocetin; and (5) adding acid to the filtrate of (3) until pH becomes 4-5, keeping the filtrate warm for 2 hours, filtering the filtrate, washing the filter residues with pure water, vacuum drying the filter residues to obtain 13-cis crocetin.

7. The method for separating trans isomeric crocetin from cis isomeric crocetin according to claim 3, wherein the alkali used is a soluble alkali solution, such as sodium hydroxide and potassium hydroxide, and the acid used is an acid that does not form a precipitate with calcium ions, such as hydrochloric acid and citric acid.

8. The method for separating trans isomeric crocetin from cis isomeric crocetin according to claim 4, wherein the alkali used is a soluble alkali solution, such as sodium hydroxide and potassium hydroxide, and the acid used is an acid that does not form a precipitate with calcium ions, such as hydrochloric acid and citric acid.

9. The method for separating trans isomeric crocetin from cis isomeric crocetin according to claim 2, wherein the method includes the following steps:

(1) placing crude crocetin and water in a beaker, adjusting pH to 7-14 with alkali, heating to dissolve the crude crocetin, filtering out insoluble matters while hot;

(2) slowly dripping calcium ions into a filtrate for crocetin calcium salt to be precipitated, keeping precipitated crocetin calcium salt warm to allow for full crystallization;

(3) filtering the filtrate;

(4) washing filter residues with ethanol, acidifying the filter residues with acid, keeping the filter residues warm, filtering the filter residues, washing the filter residues with pure water, vacuum drying the filter residues to obtain all-trans crocetin; and (5) adding acid to the filtrate of (3) for acidification, keeping the filtrate warm, filtering the filtrate, washing the filter residues with pure water, vacuum drying the filter residues to obtain cis-crocetin.

10. The method for separating trans isomeric crocetin from cis isomeric crocetin according to claim 5, wherein the alkali used is a soluble alkali solution, such as sodium hydroxide and potassium hydroxide, and the acid used is an acid that does not form a precipitate with calcium ions, such as hydrochloric acid and citric acid.

11. The method for separating trans isomeric crocetin from cis isomeric crocetin according to claim 6, wherein the alkali used is a soluble alkali solution, such as sodium hydroxide and potassium hydroxide, and the acid used is an acid that does not form a precipitate with calcium ions, such as hydrochloric acid and citric acid.

* * * * *